United States Patent
Chang

(10) Patent No.: US 9,624,290 B2
(45) Date of Patent: Apr. 18, 2017

(54) LOWERED AFFINITY ANTIBODIES AND METHODS OF MAKING THE SAME

(75) Inventor: Hsiu-Ching Chang, Lexington, MA (US)

(73) Assignee: AB BIOSCIENCES, INC., Allston, MA (US)

( * ) Notice: Subject to any disclaimer, the term of this patent is extended or adjusted under 35 U.S.C. 154(b) by 0 days.

(21) Appl. No.: 13/575,219

(22) PCT Filed: Jan. 28, 2011

(86) PCT No.: PCT/US2011/022998
§ 371 (c)(1),
(2), (4) Date: Sep. 5, 2012

(87) PCT Pub. No.: WO2011/094593
PCT Pub. Date: Aug. 4, 2011

(65) Prior Publication Data
US 2012/0329995 A1 Dec. 27, 2012

Related U.S. Application Data

(60) Provisional application No. 61/299,162, filed on Jan. 28, 2010.

(51) Int. Cl.
C07K 16/00 (2006.01)
C07K 1/00 (2006.01)
C07K 16/28 (2006.01)

(52) U.S. Cl.
CPC .......... *C07K 16/00* (2013.01); *C07K 16/2809* (2013.01); *C07K 2317/565* (2013.01); *C07K 2317/92* (2013.01); *C07K 2317/94* (2013.01)

(58) Field of Classification Search
CPC .......... A61K 2039/505; A61K 39/3955; C07K 2317/92; C07K 2317/24; C07K 2317/76
See application file for complete search history.

(56) References Cited

U.S. PATENT DOCUMENTS

| | | |
|---|---|---|
| 4,595,661 A | 6/1986 | Cragle et al. |
| 4,816,567 A | 3/1989 | Cabilly et al. |
| 4,873,316 A | 10/1989 | Meade et al. |
| 5,225,539 A | 7/1993 | Winter |
| 5,272,071 A | 12/1993 | Chappel |
| 5,565,332 A | 10/1996 | Hoogenboom et al. |
| 5,714,350 A | 2/1998 | Co et al. |
| 5,733,743 A | 3/1998 | Johnson et al. |
| 5,871,907 A | 2/1999 | Winter et al. |
| 6,350,861 B1 | 2/2002 | Co et al. |
| 2003/0219845 A1 | 11/2003 | Ruiz et al. |

FOREIGN PATENT DOCUMENTS

| | | |
|---|---|---|
| EP | 0171496 B1 | 5/1993 |
| EP | 0264166 B1 | 8/1996 |
| EP | 0125023 B2 | 3/2002 |
| WO | 8601533 A1 | 3/1986 |
| WO | 8702671 A1 | 5/1987 |
| WO | 9106667 A1 | 5/1991 |
| WO | 9945962 A1 | 9/1999 |
| WO | 00/29584 A1 | 5/2000 |
| WO | 2010088522 A2 | 8/2010 |

OTHER PUBLICATIONS

Drake et al. (Analytical Biochemistry, 2004, 328:35-43).*
Ikegami et al. (Clinical and Diagnostic Laboratory Immunology, 2003, 10:552-557).*
Giles et al. (Seminars in Arthitis and Rheumatism, 2003, 32:246-265).*
Vieira et al. (European Journal of Immunology, 1988, 18:313-316).*
Clark et al. (2006) "Affinity Enhancement of an In Vivo Matured Therapeutic antibody Using Structure-Based Computational Design," Prot. Sci. 15:949-960.
Karpusas et al. (2003) "Crystal Structure of the α1β1 Integrin I Domain in Complex With an Antibody Fab Fragment," J. Mol. Biol. 327:1031-1041.
Kusharyoto et al. (2002) "Mapping of a Hapten-Binding Site: Molecular Modeling and Site-Directed Mutagenesis Study of an Anti-Atrazine Antibody," Prot. Eng. 15(3):233-241.
Lippow et al. (2007) "Computational Design of Antibody-Affinity Improvement Beyond In Vivo Maturation," Nat. Biotechnol. 25(10):1171-1176.
Ruffaï et al. (2000) "Binding of an Antibody Mimetic of the Human Low Density Lipoprotein Receptor to Apolipoprotein E is Governed Through Electrostatic Forces," J. Biol. Chem. 275(10):7109-7116.
Reid et al. (2006) "Structure Activity Relationships of Monocyte Chemoattractant Proteins in Complex with a Blocking Antibody," Prot. Eng. Des. Select. 19(7):317-324.
Supplementary European Search Report in EP Appln. No. 11737760.6, dated Jun. 24, 2013, 9 pages.
Verhoeyen et al. (1988) "Reshaping Human Antibodies: Grafting an Antilysozyme Activity," Science 239:1534-1536.
Wada et al. (1992) "Codon Usage Tabulated From the GenBank Genetic Sequence Data," Nucleic Acids Res., 20 (Suppl):2111-2118.
Winoto et al. (1989) "A Novel, Inducible and T Cell-Specific Enhancer Located at the 3' End of the T Cell Receptor α Locus" EMBO J. 8(3):729-733.

(Continued)

*Primary Examiner* — Julie Wu
(74) *Attorney, Agent, or Firm* — John M. Garvey; Sanjukta Ghosh; DLA Piper LLP (US)

(57) ABSTRACT

The present invention provides methods for making novel, rationally designed lowered affinity antibodies. The methods of the present invention make antibodies that have variable domains that have been designed to reduce or eliminate the antigen binding activity of the parental antibody without altering the overall (3) dimensional antibody structure. Using the antibodies made using methods of the present invention in various assays allows researchers to distinguish effects that result from specific antigen-antibody interactions from other, non-specific antibody effects.

6 Claims, 11 Drawing Sheets

(56) References Cited

OTHER PUBLICATIONS

Figure 2:
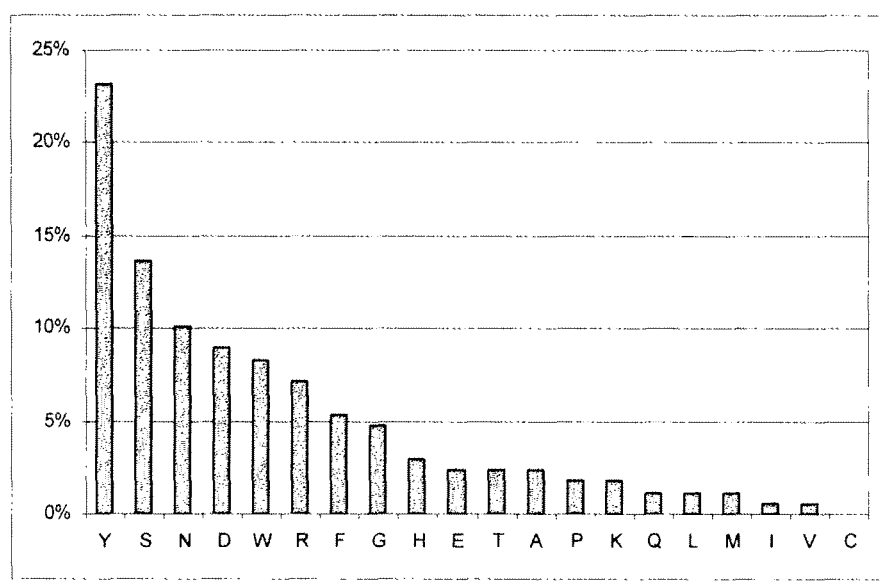
Figure 3:
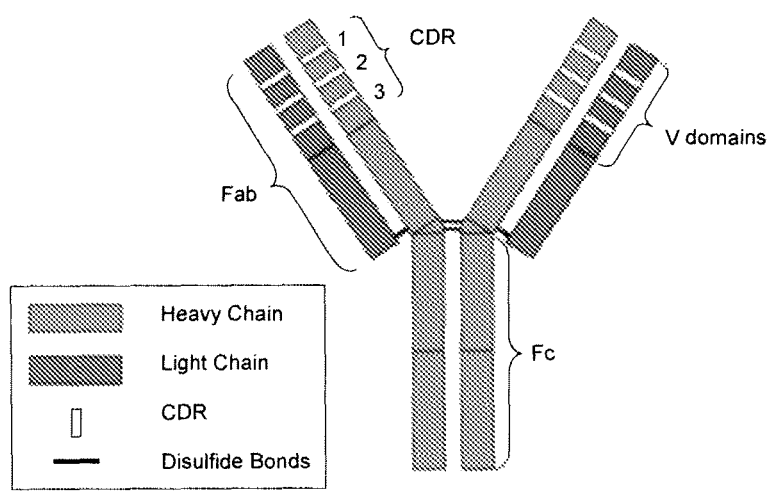
Figure 4:
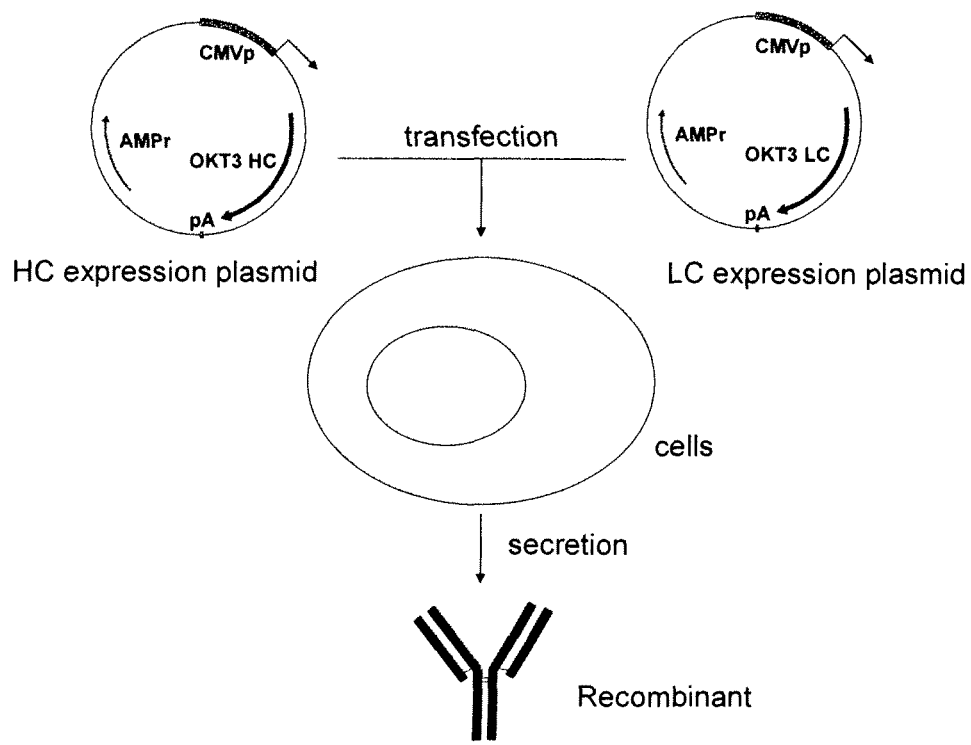
Figure 6:
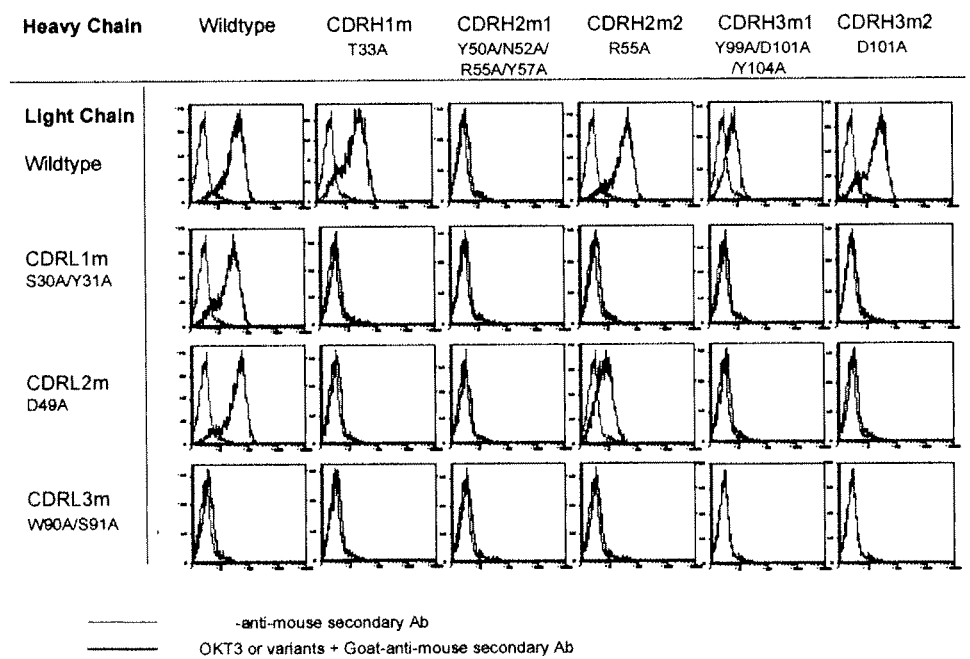

Wood et al. (1985) "The Synthesis and In Vivo Assembly of Functional Antibodies in Yeast," Nature 314:446-449.
International Search Report and Written Opinion, International Application No. PCT/US2010/022592, dated Dec. 23, 2010, 6 pages.
Valjakka et al. (2002) "Crystal Structure of an in Vitro Affinity- and Specificity-Matured Anti-Testosterone Fab in Complex with Testosterone: Improved Affinity Results From Small Structural Changes Within the Variable Domains," J. Biological Chem. 277(46):44021-44027.
McCarthy et al. (2001) "Recombinant Technology: Altering the Fine Specificity of an Anti-Legionella Single Chain Antibody by a Single Amino Acid Insertion," J. Immunol. Meth., 251:137-149.
Webster (1888) "Engineering Antibody Affinity and Specificity," Inter. J. Canc. Supp.3:13-16.
Dabbs (2002) "Diagnostic Immunohistochemistry," Churchill Livingstone, Philadelphia, PA pp. 17-19.
International Search Report and Written Opinion, International Application No. PCT/US2011/022998, dated Oct. 27, 2011, 9 pages.
Winkler et al. (2000) "Changing the Antigen Binding Specificity by Single Point Mutations of an Anti-p24 (HIV-1) Antibody," J. Immunol. 165:4505-4514.
Amann et al. (1988) "Tightly Regulated tac Promoter Vectors Useful for the Expression of Unfused and Fused Proteins in *Escherichia coli*," Gene, 69:301-315.
Armour et al. (2003) "Differential Binding to Human FcγRIIa and FcγRIIb Receptors by Human IgG Wildtype and Mutant Antibodies," Mol. Immunol., 40:585-593.
Baldari et al. (1987) "A Novel Leader Peptide Which Allows Efficient Secretion of a Fragment of Human Interleukin 1β in *Saccharomyces cerevisiae*," EMBO J., 6(1):229-234.
Banerji et al. (1983) "A Lymphocyte-Specific Cellular Enhancer is Located Downstream of the Joining Region in Immunoglobulin Heavy Chain Genes," Cell, 33:729-740.
Beidler et al. (1988) "Cloning and High Level Expression of a Chimeric Antibody with Specificity for Human Carcinoembryonic Antigen," J. Immunol., 141(11):4053-4060.
Better et al. (1988) "*Escherichia coli* Secretion of an Active Chimeric Antibody Fragment," Science, 240:1041-1043.
Bird et al. (1988) "Single-Chain Antigen-Binding Proteins," Science, 242:423-426.
Byrne et al. (1989) "Multiplex Gene Regulation: A Two-Tiered Approach to Transgene Regulation in Transgenic Mice," Proc. Natl. Acad. Sci. USA, 86:5473-5477.
Camper et al. (1989) "Postnatal Repression of the α-Fetoprotein Gene is Enhancer Independent," Genes & Develop., 3:537-546.
Capel et al. (1994) "Heterogeneity of Human IgG Fc Receptors," Immunomethods 4:25-34.
Chaiken (1981) "Semisynthetic Peptides and Proteins," in Critical Reviews in Biochemistry and Molecular Biology, 11:255-301.
Chothia et al. (1987) "Canonical Structures for the Hypervariable Regions of Immunoglobulins," J. Mol. Biol., 196:901-917.
Daëron (1997) "Fc Receptor Biology," Annu. Rev. Immunol., 15:203-234.
Edlund et al. (1985) "Cell-Specific Expression of the Rat Insulin Gene: Evidence for Role of Two Distint 5' Flanking Elements," Science, 230:912-916.
Goeddel (1990) "Systems for Heterologous Gene Expression," Methods in Enzymol., 185:3-7.
Gottesman (1990) "Minimizing Proteolysis in *Escherichia coli*: Genetic Solutions," Methods in Enzymol. 185:119-128.
Gutte et al. (1969) "The Total Synthesis of an Enzyme With Ribonuclease A Activity," in Communications to the Editor, J. Am. Chem. Soc. 91(2):501-502.
Huston et al. (1988) "Protein Engineering of Antibody Binding Sites: Recovery of Specific Activity in an Anti-digoxin Single-Chain Fv analogue Produced in *Escherichia coli*," Proc. Natl. Acad. Sci. USA, 85:5879-5883.
Jones et al. (1986) "Replacing the Complementarity-Determining Regions in a Human Antibody With Those From a Mouse," Nature 321:552-525.
Kaiser et al. (1989), "Peptide and Protein Synthesis by Segment Synthesis-Condensation," Science 243:187-192.
Kanda et al., (2006) "Comparison of Biological Activity Among Nonfucosylated Therapeutic IgG1 Antibodies With Three Different N-Linked Fc Oligosaccharides: the High-Mannose, Hybrid, and Complex Types," Glycobiology, 17 (1):104-118.
Kaufman et al. (1987) "Translational Efficiency of Polycistronic mRNAs and their Utilization to Express Heterologous Genes in Mammalian Cells," EMBO J., 6(1):187-193.
Kent (1988) "Chemical Sy8nthesis of Peptides and Proteins," Annu. Rev. Biochem. 57:957-989.
Kessel et al. (1990) "Murine Development Control Genes," Science 249:374-379.
Kjer-Nielsen et al. (2004) "Crystal Structure of the Human T Cell Receptor CD3εγ Heterodimer Complexed to the Therapeutic mAb OKT3," Proc Natl Acad Sci USA 101(20):7675-7680.
Kurjan et al. (1982) "Structure of a Yeast Pheromone Gene (MGα): A Putative α-Factor Precursor Contains Four Tandem Copies of Mature α-Factor," Cell 30:933-943.
Liu et al. (1987) "Chimeric Mouse-Human IgG1 Antibody That Can Mediate Lysis of Cancer Cells," Proc. Natl. Acad. Sci. USA, 84:3439-3443.
Liu et al. (1987) "Production of a Mouse-Human Chimeric Monoclonal Antibody to CD20 With Potent Fc-Dependent Biologic Activity," J. Immunol., 139(10):3521-3526.
Luckow et al. (1989) "High Level Expression of Nonfused Foreign Genes With Autographa Californica Nuclear Polyhedrosis Virus Expression Vectors," Virology, 170:31-39.
MacCullum et al. (1996) "Antibody-Antigen Interactions: Contact Analysis and Binding Site Topography," J. Mol. Biol., 262:732-745.
Merrifield (1986) "Solid Phase Synthesis," Science, 232:341-347.
Midtvedt et al. (2003) "Individualized T Cell Monitored Administration of ATG Versus OKT3 in Steroid-Resistant Kidney Graft Rejection" Clin. Transplant.,17: 69-74.
Morrison (1985) "Transfectomas Provide Novel Chimeric Antibodies," Science 229:1202-1207.
Nishimura et al. (1987) "Recombinant Human-Mouse Chimeric Monoclonal Antibody specific for Common Acute Lymphocytic Leukemia Antigen," Cancer Res. 47:999-1005.
Pinkert et al. (1987) "An Albumin Enhancer Located 10 kb Upstream Functions Along With its Promoter to Direct efficient, Liver-Specific Expression in Transgenic Mice," Genes & Dev. 1:268-277-276.
Queen et al. (1983) "Immunoglobulin Gene Transcription is Activated by Downstraem Sequence Elements," Cell 33:741-748.
Queen et al. (1989) "A Humanized Antibody That Binds to the Interleukin 2 Receptor," Proc. Natl. Acad. USA, 86:10029-10033.
Raju (2008) "Terminal Sugars of Fc Glycans Influence Antibody Effector Functions of IgGs," Current Opinion in Immunol., 20:471-478.
Ravetch et al. (1991) "Fc Receptors," Annu. Rev. Immunol., 9:457-492.
Riechmann et al. (1998) "Reshaping Human Antibodies for Therapy," Nature 332:323-327.
Roopenian et al. (2007) "FcRn: The Neonatal Fc Receptor Comes of Age," Nat. Rev. Immunol. 7:715-725.
Schultz et al. (1987) "Expression and Secretion in Yeast of a 400-kDa Envelope Glycoprotein Derived From Epstein-Bar Virus," Gene 54:113-123.
Shaw et al. (1988) "Mouse/Human Chimeric Antibodies to a Tumor-Associated Antigen : Biologic Activity of the four Human IgG Subclasses," J. Natl. Cancer Inst. 80(19):1553-1559.
Smith et al. (1983) "Production of Human Beta Interferon in Insect Cells Infected With a Baculovirus Expression Vector," Mol. & Cell. Biol., 3(12):2156-2165.

(56) References Cited

OTHER PUBLICATIONS

Smith et al. (1988) "Single-Step Purification of Polypeptides Expressed in *Escherichia coli* as Fusions With Glutathione S-Transferase," Gene 67:31-40.
Studier et al. (1990) "[6] Use of T7 RNA Polymerase to Direct Expression of Cloned Genes," Methods in Enzymol., 185:60-89.
Sun et al. (1987) "Chimeric Antibody With Human Constant Regions and Mouse Variable Regions Directed Against Carcinoma-Associated Antigen," Proc. Natl. Acad. Sci. USA, 84:214-218.
Talbot et al. (1987) "Catabolism of Homologous Murine Monoclonal Hybridoma IgG Antibodies in Mice," Immuno., 60:485-489.
Thorpe et al. (1982) "The Preparation and Cytotoxic Properties of Antibody-Toxin Conjugates," Immunol. Rev., 62:119-158.
Keitel et al., (1997), "Crystallographic Analysis of Anti-p24 (HIV-1) Monoclonal Antibody Cross-Reactivity and Polyspecificity", Cell Press, 91, 811-820.
Abraham et al. In vivo metabolism of a monoclonal IgG cryoglobulin. Clin. Exp. Immunol. 1979;35:89-95.
Dul et al. A conditional secretory mutant in an Ig L chain is caused by replacement of tyrosine/phenylalanine 87 with histidine. J. Immunol. 1992;149(6):1927-1933.
Hammond et al. Quality control in the secretory pathway. Curr. Opin. in Cell Biol. 1995;7:523-529.
Rosenberg. Effects of Protein Aggregates: An Immunologic Perspective. AAPS J. 2006;8(3)Art.59:E501-E507.
Sassen et al. Immunogenic Potency of Human γ-Globulin in Mice. Immunol. 1968;14:247-256.
Sigounas et al. Half-Life of Polyreactive Antibodies. J. Clin. Immunol. 1994;14(2):134-140.
Talbot et al. Catabolism of homologous murine monoclonal hybridoma IgG antibodies in mice. Immunol. 1987;60:485-489.

\* cited by examiner

Generation of Ab variants with silenced CDRs

```
              ┌──────────────────┐
              │ Antibody selected │
              └──────────────────┘
                       │
                       ▼
              ┌──────────────────┐
              │ CDR regions identified │
              └──────────────────┘
                 │            │
                 ▼            ▼
    ┌──────────────────┐   ┌──────────────────┐
    │ Atomic structure │   │ No structure     │
    │ published        │   │ available        │
    └──────────────────┘   └──────────────────┘
             │                     │
             ▼                     ▼
   ┌──────────────────┐  ┌──────────────────────────────────┐
   │ Identification of│  │ Identification of potential Ag-  │
   │ Ag-contacting    │  │ contacting residues based on     │
   │ residues         │  │ historical survey (table/next    │
   │                  │  │ page)                            │
   └──────────────────┘  └──────────────────────────────────┘
                       │
                       ▼
           ┌────────────────────────────────┐
           │ Engineering and expression of variants │
           └────────────────────────────────┘
                       │
                       ▼
           ┌────────────────────────────────┐
           │ Ag-binding activity tests for  │
           │ Identification of Ab variants  │
           │ with CDRs silenced             │
           └────────────────────────────────┘
```

Figure 1

Antibody production of OKT3 and variants in 293 T transfection (ug/ml)

| Light Chain | Chain | Wild type NA | CDRH1m T33A | CDRH2m1 Y50A/N52A/ R55A/Y57A | CDRH2m2 R55A | CDRH3m1 Y99A/D101A / Y104A | CDRH3m2 D101A |
|---|---|---|---|---|---|---|---|
| Wild type | NA | 5.8 | 6.7 | 2.8 | 3.4 | 2.5 | 1.4 |
| CDRL1m | S30A/Y31A | 4.7 | 7.7 | 2.9 | 4.1 | 3.0 | 2.9 |
| CDRL2m | D49A | 2.8 | 2.3 | 2.1 | 1.2 | 1.3 | 1.0 |
| CDRL3m | W90A/S91A | 4.3 | 2.9 | 3.5 | 2.5 | 3.3 | 1.9 |

Figure 5

Mutations within the CDRs abolish OKT3 binding to human PBMC

| Heavy Chain | Wildtype | CDRH1m<br>T33A | CDRH2m1<br>Y50A/N52A/<br>R55A/Y57A | CDRH2m2<br>R55A | CDRH3m1<br>Y99A/D101A<br>/Y104A | CDRH3m2<br>D101A |
|---|---|---|---|---|---|---|
| Light Chain<br>Wildtype | | | | | | |
| CDRL1m<br>S30A/Y31A | | | | | | |
| CDRL2m<br>D49A | | | | | | |
| CDRL3m<br>W90A/S91A | | | | | | |

——— -anti-mouse secondary Ab
——— OKT3 or variants + Goat-anti-mouse secondary Ab

Figure 7

Pharmacokinetics of OKT3-NC [seq 26x47] in C57B6 mice

T1/2 = 13.75 days

| Y (ng/ml) | X (hour) |
|---|---|
| 20,000 | 214.75 |
| 10,000 | 544.82 |

# LOWERED AFFINITY ANTIBODIES AND METHODS OF MAKING THE SAME

CROSS-REFERENCE TO RELATED APPLICATIONS

This application claims priority to the benefit of U.S. Provisional Application 61/299,162, filed on Jan. 28, 2010, the entire contents of which are incorporated herein by reference.

SEQUENCE LISTING

The instant application contains a Sequence Listing which has been submitted in ASCII format via EFS-Web and is hereby incoporated by reference in its entirety. Said ASCII copy, created on Aug. 15, 2012, is named ABB003.txt and is 4,025 bytes in size.

BACKGROUND OF THE INVENTION

Because of their ability to bind an antigen with a high degree of specificity, monoclonal antibodies are widely used as research, diagnostic, and therapeutic reagents. In addition to their specific binding to an antigen, monoclonal antibodies may activate the complement system and effector cells through their Fc region. In order to properly interpret an antibody's biological properties, proper controls are essential. Without proper controls, it is difficult to establish a causal relationship between an antibody's specific binding activity and the biochemical and biological effects of the antibody.

Control monoclonal antibodies currently in use include: 1. antibodies secreted by naturally occurring plasmacytoma, with no known target antigens; 2. antibodies raised against antigens from evolutionarily distant species, such as KLH (keyhole limpet hemocyanin); 3. antibodies reactive with a known target antigen that is distinct from the antigen of interest.

In each of these cases, the control antibodies used have a poorly defined variable domain and uncertain antigen specificities. And in the third case, there remains the issue of cross reactivity. Because of this, it is not uncommon to encounter problems such as cross reactivity or non-specific binding when currently available control antibodies are used. Furthermore, due to the lack of an ideal control antibody, research is often performed using formulation vehicles, such as normal saline, as a control. In such cases, it is difficult, if not impossible, to distinguish whether an observed biochemical and/or biological effect is a direct result of the specific antigen/antibody interaction, or a result of nonspecific effects, such as interactions and biological effects of other parts of the antibody molecule or contaminants present in the antibody preparation, such as the host cell proteins. For at least these reasons, there is currently a great need for improved, rationally designed control antibodies.

SUMMARY OF THE INVENTION

In one aspect, the invention provides a method for producing a complementarity determining region (CDR) with reduced binding capability comprising the steps of (a) identifying from within a CDR polypeptide, at least one binding amino acid, which is capable of an interaction with an antigen; and (b) altering the at least one binding amino acid within the CDR polypeptide so that the resulting CDR has a reduced ability in binding the antigen. In some embodiments the CDR is located within an antibody or antibody fragment. In some embodiments the method also includes the step of validating a loss of antigen binding. The validation step may be accomplished by FACS analysis.

In another aspect, the invention provides a method for producing an antibody or antibody fragment with reduced binding capability comprising the steps of (a) identifying from within an antibody or antibody fragment, at least one binding amino acid, which is capable of an interaction with an antigen; and (b) altering the at least one binding amino acid within the antibody or antibody fragment so that the resulting antibody has a reduced ability in binding the antigen. In some embodiments the method also includes the step of validating a loss of antigen binding. The validation step may be accomplished by FACs analysis.

In some embodiments the interaction is a hydrogen bond, a salt bridge, and/or a Van der Waal's force. In certain embodiments the binding amino acid is aspartic acid, glutamic acid, lysine, arginine, serine, threonine, tyrosine, asparagine, histidine or glutamine. In other embodiments the binding amino acid is tyrosine, serine, asparagine, aspartic acid, tryptophan, arginine, phenylalanine or glycine. In some embodiments the binding amino acid is replaced with a non-binding amino acid. In some embodiments the non-binding amino acid is alanine, valine, leucine, isoleucine, proline or methionine.

In certain embodiments of the invention the step of identifying the binding amino acid is performed by analyzing a crystal structure depicting a complex between the CDR and the antigen.

In another aspect, the invention includes the antibody or antibody fragment generated using the methods of the invention. In some embodiments, the antibody or antibody fragment of the invention has a dissociation constant ($K_D$) of greater than or equal to about $10^{-7}$. In some embodiments the antibody or antibody fragment of the invention is a whole immunoglobulin molecules, a scFv, an Fab fragment, an Fab' fragment, an F(ab')2, an Fd fragment, an Fv or a disulfide linked Fv.

BRIEF DESCRIPTION OF THE DRAWINGS

FIG. 1 shows a flow chart depicting the making of control antibodies of the invention.

FIG. 2 shows the frequency that specific CDR amino acids are involved in antibody-antigen interactions.

FIG. 3 shows an exemplary schematic diagram of an antibody structure, including the Fv domain, the Fab domain and the Fc domain.

FIG. 4 shows a schematic representation of an exemplary method of recombinant antibody production.

FIG. 5 shows antibody production of OKT3 and some exemplary control antibodies of the invention.

FIG. 6 shows FACS plots demonstrating binding of some exemplary control antibodies of the invention to human Jurkat cells.

FIG. 7 shows FACS plots demonstrating binding of some exemplary control antibodies of the invention to human PBMC.

FIG. 8 shows a map of the pME-wtOKT3 HC vector that encodes the OKT3 heavy chain.

FIG. 9 shows a map of the pME-wtOKT3 LC vector that encodes the OKT3 light chain.

FIG. 10 shows the binding of OKT3 and OKT3 variant to Jurkat cells.

FIG. 11 shows a pharmacokinetics of the variant antibody.

DETAILED DESCRIPTION OF THE INVENTION

The present invention provides novel, lowered affinity antibodies, having well characterized variable domains that reduce or eliminate antigen binding without substantially altering the three dimensional structure of the antibody. In order for the present invention to be more readily understood, certain terms and phrases are defined below as well as throughout the specification.

The term "antibody" is well understood in biological and biomedical field and commonly refers to whole antibodies and any antibody fragment, or single chain thereof. Antibodies are glycoproteins secreted by specialized B lymphocytes known as plasma cells. They are also referred to as immunogobulins (Ig) because they contain a common structural domain found in many proteins. Antibodies most likely comprise two heavy (H) chains and two light (L) chains typically connected by disulfide bonds, or an antigen binding portion thereof. Each heavy chain is comprised of a heavy chain variable region ($V_H$) and a heavy chain constant region. Each light chain is also comprised of a variable region ($V_L$) and a constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

The present invention includes antibody fragments as well. Examples of antibody fragments include (i) a Fab fragment, a monovalent fragment consisting of the $V_H$, $V_L$, CL and CH1 domains; (ii) a $F(ab')_2$ fragment, a bivalent fragment comprising two Fab fragments linked by disulfide bridges at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. As used herein, "antibody" and "antibody fragments" are used interchangeably to describe the invention unless specifically stated otherwise.

The term "hypervariable region," "HVR," or "HV," refers to the regions of an antibody-variable domain that are hypervariable in sequence and form structurally defined loops. Generally, antibodies comprise six HVRs; three in the VH (H1, H2, H3), and three in the VL (L1, L2, L3). In an antibody molecule, the three HVRs of a VH domain and the three HVRs of a VL domain are brought together in three-dimensional structure to form an antigen binding surface. Because these sequences form a surface that is complementary to the three dimensional structure of the target antigen, the HVRs are also known as complementarity-determining regions (CDRs).

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," $5^{th}$ Edition, U.S. Department of Health and Human Services, 1992; Chothia et al., J. Mol. Biol., 1987, 196: 901; and MacCallum et al., J. Mol. Biol., 1996, 262: 732, each of which is incorporated by reference in its entirety).

"Framework region" or "FR" residues are those variable-domain residues other than the HVR residues as herein defined. Exemplary framework regions are provided as SEQ ID NOs. 15-22.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include IgG, IgM, IgA, IgD and IgE.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the Fc gamma RI, Fc gamma RII, and Fc gamma RIII subclasses, including allelic variants and alternatively spliced forms of these receptors, Fc gamma RII receptors include Fc gamma RIIA (an "activating receptor") and Fc gamma RIIB (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain Inhibiting receptor Fc gamma RIIB contains an immunoreceptor tyrosine-based inhibition motif (ITIM) in its cytoplasmic domain. (see M. Daëron, Annu Rev. Immunol. 15:203-234 (1997). FcRs are reviewed in Ravetch and Kinet, Annu Rev. Immunol. 9: 457-92 (1991); Capel et al., Immunomethods 4: 25-34 (1994); and de Haas et al., J. Lab. Clin. Med. 126: 330-41 (1995). Other FcRs, including those binding to other isotypes as well as those to be identified in the future, are encompassed by the term "FcR" herein.

Antibodies may be xenogeneic, allogeneic, or syngeneic; or modified forms thereof (e.g., humanized, chimeric, etc.). Antibodies may also be fully human. The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising human heavy and light chain transgenes fused to an immortalized cell.

In some embodiments of the invention, antibodies, or fragments thereof, are modified to reduce or eliminate potential glycosylation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis (see http://www.cbs.dtu.dk/services/NetNGlyc/ for predicting N-linked glycosylation sites) and http://www.cbs.dtu.dk/services/NetOGlyc/ for predicting O-linked glycosylation sites). Additional methods for altering glycosylation sites of antibodies are described in U.S. Pat. Nos. 6,350,861 and 5,714,350. Further, antibody glycosylation can be influenced by the cell in which it is produced, the conformation of an antibody and the cell culture conditions. The preferred cell expression system of the invention is human cell expression system.

The term "humanized antibody" refers to an antibody that consists of the CDR of antibodies derived from mammals other than human, and the FR region and the constant region of a human antibody. A humanized antibody is useful as an effective component in a therapeutic agent since antigenicity of the humanized antibody in human body is lowered. It is an objective of the present invention to design lowered affinity antibodies to humanized antibodies in the context of therapeutic applications.

The term "recombinant antibody" includes all antibodies that are prepared, expressed, created or isolated by recombinant means, such as (a) antibodies isolated from an animal (e.g., a mouse) that is transgenic or transchromosomal for immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such recombinant antibodies have variable and constant regions derived from germline and/or non-germline immunoglobulin sequences. In certain embodiments, however, such recombinant antibodies can be subjected to in vitro mutagenesis (or, when an animal transgenic for Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the germline repertoire in vivo.

The term "bispecific monoclonal antibody" refers to a monoclonal antibody having dual specificity in their binding arms to two different types of antigen. Bispecific monoclonal antibodies do not occur naturally; they have to be made with recombinant DNA or cell fusion technology. With this approach, it is possible for such an antibody to simultaneously bind to a cytotoxic cell (using a receptor like CD3) and a cancer target cell (like CD19), leading to more efficient killing of target cancer cells. It is the objective of the present invention to design lowered affinity antibodies to bispecific monoclonal antibodies such that one or both arms of the biospecific antibody will have reduced or eliminated affinity to an antigen.

The term "$K_D$" is intended to refer to the dissociation equilibrium constant of a particular antibody-antigen interaction. The measure of the binding strength of an antibody for a monovalent epitope is referred to as affinity. In some instances, antibodies can form multivalent interactions with antigen. In such cases, the apparent dissociation equilibrium constant of an antibody/antigen interaction may vary from the monovalent dissociation constant.

Affinity varies depending on the non-covalent bonds that exist between the antigen combining site on the antibody and the antigenic determinant or epitope of the specific antigen. In a typical situation, antibodies are used for their specific binding properties and the antibody binds with an affinity ($K_D$) of approximately less than $10^{-7}$ M, such as approximately less than $10^{-8}$ M, $10^{-9}$ M or $10^{-10}$ M or even lower when determined, for example, by surface plasmon resonance (SPR) technology in a BIACORE instrument using recombinant proteins as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen". An antibody that has "lowered affinity" refers to a $K_D$ of approximately greater than $10^{-7}$ M, such as approximately 10, or 100, or 1000 fold greater than $10^{-7}$ M. It is the objective of the present invention to design an antibody with little or no specific binding to an antigen. In some embodiments the antibodies of the invention have a dissociation constant ($K_D$) of greater than or equal to about $10^{-7}$. More preferably, the antibodies of the invention have a dissociation constant ($K_D$) of greater than or equal to about $10^{-6}$. Most preferably, the antibodies of the invention have no detectable specific binding towards a defined antigen.

Depending on the Ig class, up to five structural molecules may be combined to form any one antibody. In mammals, there are five classes of Ig (IgG, IgM, IgA, IgD, and IgE); and in avians, there are three classes (IgY, IgM, and IgE). In select mammals, IgG and IgA are further subdivided into subclasses, referred to as isotypes, due to polymorphisms in the conserved regions of the heavy chain.

The term "nucleic acid molecule" or "polynucleotide" is intended to include DNA molecules and RNA molecules. A nucleic acid molecule may be single-stranded or double-stranded, but preferably is double-stranded DNA.

The present invention also encompasses "conservative sequence modifications" of the sequences set forth in the figures, including nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequence set forth in the figures by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Accordingly, antibodies encoded by the heavy and light chain variable region nucleotide sequences disclosed herein and/or containing the heavy and light chain variable region amino acid sequences disclosed herein include substantially similar antibodies encoded by or containing similar sequences which have been conservatively modified. Further discussion as to how such substantially similar antibodies can be generated based on the sequences (i.e., heavy and light chain variable regions) disclosed herein is provided below.

The nucleic acid compositions of the present invention may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

Various aspects of the invention are described in further detail in the following subsections.

I. Lowered Affinity Antibodies

Lowered affinity antibodies of the present invention are antibodies that were rationally designed to eliminate or reduce binding to an antigen. A currently preferred lowered affinity antibody is one that resembles the wild type (native) antibody in every respect except for the CDR region and shows little discernable 3 dimensional structural change relative to the wild type antibody. An exemplary antibody is one that demonstrates a decreased binding affinity to an antigen by 10 fold. Preferably, a lowered affinity antibody binds to an antigen with a decreased binding affinity to an antigen by 100 fold. More preferably, a lowered affinity antibody binds to an antigen with a decreased binding affinity to an antigen by 1000 fold. Most preferably, a lowered affinity antibody shows no substantial binding to an antigen, and no specific binding to an antigen is detectible over the background binding levels. The affinity can be measured by common experimental methods including surface Plasmon resonance, or radio ligand binding assay, or flow cytometry. Lowered affinity antibodies of the present invention are useful as control reagents for their wild type (native) counterpart that retains specific binding to an antigen in many in vivo and in vitro applications that involve the use of antibodies.

Lowered affinity antibodies of the invention can be produced using a variety of known techniques, such as the recombinant DNA techniques and other standard molecular and cell biology techniques.

Recombinant lowered affinity antibodies can be made using recombinant DNA techniques and gene transfection methods well known in the art (Morrison, S. (1985) Science 229: 1202). For example coding sequences, antibody-encoding polynucleotides with known antigen specificity can be amplified by standard molecular biology techniques (e.g. polymerase chain reaction) and ligated into an expression vector (e.g. pME). Mutations can be introduced into the expression vector using standard site directed mutagenesis techniques in order to disrupt antigen binding of the encoded antibodies. Expression vectors encoding the mutated antibody heavy and light chain genes can be transfected into host cells (e.g. 293T cells, CHO-cells) using techniques known in the art (e.g. calcium phosphate precipitation, electroporation, lipofection).

Following introduction of the expression vectors into the host cells, cells will begin to produce and secret mutated antibodies into the culture media. Long term, large scale antibody production can be achieved, for example, by identifying and selecting cells expressing the mutated antibody. Recombinant antibodies can be isolated and purified from these culture supernatants and/or cells using techniques known in the art. Alternatively, mutated antibodies can be produced in other expression systems or complete organisms or can be produced synthetically.

In another embodiment lowered affinity antibodies can be generated as chimeric antibodies in which the variable regions of the antibody heavy and/or light chains are fused to constant domains from various species.

In addition, humanized lowered affinity antibodies can be made according to standard protocols such as those disclosed in U.S. Pat. No. 5,565,332. In another embodiment, antibody chains can be produced by recombination between vectors comprising nucleic acid molecules encoding a fusion of a polypeptide chain of a specific antibody chain and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743.

Lowered affinity antibodies can be produced using recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239: 1534; and Beidler et al. (1988) J. Immunol. 141:4053-4060.

In still another aspect of the invention, partial or known antibody sequences can be used to generate and/or express lowered affinity antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of a specific antibody by constructing expression vectors that include CDR sequences from the specific antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse).

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem.); and, restriction sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for this use are known in the art and include the plasmids provided in the Examples section below. Similar plasmids can be constructed for expression of other heavy chain isotypes, or for expression of antibodies comprising lambda light chains. Antibodies of the present invention thus also include various isotypes (IgG, IgE, IgA, IgM, and IgD) of antibodies from different species.

In yet another aspect of the invention, lowered affinity antibodies can be generated by using phage and/or yeast display technology. For example, the variable regions of heavy (VH) and light chain (VL) of an antibody with known antigen specificity can be fused as a single chain Fv fragment and displayed on a phage and/or yeast surface. Displaying such scFv will exhibit strong binding activity to its target antigen. Random mutagenesis can be performed on one or more of the CDRs of the Fv Fragment, thereby constructing a phage library. The library can be selected for clones that no longer exhibit antigen binding, thereby identifying CDR mutations that eliminate or reduce antigen binding.

Validation of a reduction and/or elimination of antigen specificity of lowered affinity antibodies can be done using methods known in the art. Techniques useful for a demonstration of reduced antigen binding include, for example, FACs analysis, immunoblotting, competitive binding assays, immunohistochemistry, and surface plasmon resonance technology. Amino acids responsible for interactions between an antigen and an antibody (binding amino acids) can be identified, for example, by analysis of the interactions between the amino acids on the antigen surface and amino acids in the CDR regions of the antibody. The nature of these interactions can be classified into 3 major categories, van der Waal's forces, hydrogen bonds, and the salt bridges. Interactions are most commonly formed between antigenic determinants and CDR amino acid side chains, though hydrogen bonds may also be mediated by water molecules between antigen determinants and CDR amino acid side chains. CDR amino acids most frequently involved in Van der Waal's force interaction include Ala, Phe, Ile, Leu, Asn, Pro, Gln, Val, Trp, and Tyr. CDR amino acids that most frequently form salt bridges include Asp, Glu, Arg, and Lys. CDR amino acids most frequently involved in hydrogen bond interactions include Asp, Glu, His, Lys, Arg, Ser, and Tyr. Analysis of CDR amino acids involved in antigen interactions reveals a pattern whereby certain amino acids are more likely to be involved in antibody/antigen interactions than others. Binding amino acid/antigen interactions were determined either by site directed mutagenesis (mutational) of specific amino acids within the CDR regions, or through analysis of crystal structures of the antigen-antibody complexes (x-tal). The antibodies used in this analysis are listed in Table 1.

TABLE 1

Antibodies used in antibody/antigen interaction analysis

| Antibody | Antigen | Method |
|---|---|---|
| OKT3[1] | CD3 | X-tal |
| 23C3[2] | Osteopontin | X-tal |
| 5c8[3] | CD154 | X-tal |
| 7G10[4] | Interleukin-23 | X-tal |
| B13I2[5] | myohemerythrin C-helix peptide | Mutational |
| Fab4-4-20[5] | Single strand DNA | Mutational |
| FabD1.3[5] | Hen egg lysozyme | Mutational |
| H57[6] | CD8 | X-tal |
| HyHEL-10[5] | Hen egg lysozyme | Mutational |
| HyHEL-5[5] | Hen egg lysozyme | Mutational |
| K411B[7] | Atrazine | Mutational |
| McPC603[5] | Phosphocholine | Mutational |
| Rituxan[8] | CD20 | X-tal |
| YTS156[9] | CD8 | X-tal |

[1]Crystal structure of the human T cell receptor CD3 epsilon gamma heterodimer complexed to the therapeutic mAb OKT3. Kjer-Nielsen L, Dunstone M A, Kostenko L, Ely L K, Beddoe T, Mifsud N A, Purcell A W, Brooks A G, McCluskey J, Rossjohn J. (2004) Proc Natl Acad Sci USA. 101: 7675-7680.
[2]Molecular basis of recognition of human osteopontin by 23C3, a potential therapeutic antibody for treatment of rheumatoid arthritis. Du J, Hou S, Zhong C, Lai Z, Yang H, Dai J, Zhang D, Wang H, Guo Y, Ding J. (2008) J Mol Biol. 382: 835-842
[3]Structure of CD40 ligand in complex with the Fab fragment of a neutralizing humanized antibody. Karpusas M, Lucci J, Ferrant J, Benjamin C, Taylor F R, Strauch K, Garber E, Hsu Y M. (2001) Structure. 4; 9: 321-329.
[4]Crystal structures of the pro-inflammatory cytokine interleukin-23 and its complex with a high-affinity neutralizing antibody. Beyer B M, Ingram R, Ramanathan L, Reichert P, Le H V, Madison V, Orth P. (2008) J Mol Biol. 382: 942-955.
[5]Structure, function and properties of antibody binding sites. Mian I S, Bradwell A R, Olson A J. (1991) J Mol Biol. 217: 133-151.
[6]Atomic structure of an alphabeta T cell receptor (TCR) heterodimer in complex with an anti-TCR fab fragment derived from a mitogenic antibody. Wang J, Lim K, Smolyar A, Teng M, Liu J, Tse A G, Liu J, Hussey R E, Chishti Y, Thomson C T, Sweet R M, Nathenson S G, Chang H C, Sacchettini J C, Reinherz E L. (1998) EMBO J. 17: 10-26.
[7]Mapping of a hapten-binding site: molecular modeling and site-directed mutagenesis study of an anti-atrazine antibody. Kusharyoto W, Pleiss J, Bachmann T T, Schmid R D. Protein Eng. (2002) 15: 233-41.
[8]Structural basis for recognition of CD20 by therapeutic antibody Rituximab. Du J, Wang H, Zhong C, Peng B, Zhang M, Li B, Huo S, Guo Y, Ding J. (2007) J Biol Chem. 282: 15073-80.
[9]The Crystal Structure of CD8 in Complex with YTS156.7.7 Fab and Interaction with Other CD8 Antibodies Define the Binding Mode of CD8 alphabeta to MHC Class I. Shore D A, Issafras H, Landais E, Teyton L, Wilson I A. (2008) J Mol. Biol. In press Analysis of the antibody/antigen interactions reveals that Tyr interacts with antigen determinants most frequently, accounting for about a quarter of all interactions, followed by Ser, which is responsible for about 14% of the interactions (Table 2, FIG. 2). Together with Asn and Glu, these four amino acids accounted for more than half (56%) of all contacts. Such bias in antigen-contacting CDR amino acids allows the generation of an algorithm for identifying CDR amino acids that are most likely to interact with antigen determinants. Briefly, CDR regions are identified based on methods known in the art and described above. For an antibody with a known crystal structure, the structure can be analyzed to determine the CDR residues that contact antigen determinants. For an antibody whose structure is not known or available, CDR residues likely to be involved in antigen interactions can be determined based on the frequencies shown in the Table 2 and FIG. 3.

Lowered affinity antibodies of the current invention can be generated by the alteration of one or more amino acids involved in antibody/antigen contacts (binding amino acids) in an antibody capable of binding an antigen. Binding amino acids can be identified using any technique known in the art or described herein, including but not limited to, crystal structure analysis and use of amino acid "contact frequency statistics" (Table 2 and FIG. 3). In some embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 binding amino acids are altered. In some embodiments, at least 10%, 25%, 50%, 60%, 70%, 80%, 85%, 90%, 95%, or 100% of the binding amino acids are altered. Alteration of the binding amino acids can be performed using any method that disrupts the ability of the binding amino acid to form a contact with an antigen, including, but not limited to replacement of the binding amino acid with a non-binding amino acid and/or deletion of the binding amino acid. Binding amino acids can also be altered through deletions, replacements, or insertions to the amino acid sequence either upstream or downstream of the binding amino acid that disrupt the ability of the binding amino acid to contact an antigen.

TABLE 2

The frequency of CDR amino acids contacting antigen determinants.

| AA | CDRL1 | CDRL2 | CDRL3 | CDRH1 | CDRH2 | CDRH3 | TOTAL | % |
|----|-------|-------|-------|-------|-------|-------|-------|-----|
| Y  | 11    | 3     | 3     | 6     | 8     | 8     | 39    | 23% |
| S  | 3     |       | 6     | 2     | 11    | 1     | 23    | 14% |
| N  | 4     |       | 3     | 1     | 7     | 2     | 17    | 10% |
| D  | 2     | 3     | 2     | 2     | 3     | 3     | 15    | 9%  |
| W  |       |       | 5     | 4     | 2     | 3     | 14    | 8%  |
| R  | 1     |       | 1     | 1     | 5     | 4     | 12    | 7%  |
| F  | 2     |       | 4     |       | 1     | 2     | 9     | 5%  |
| G  | 1     |       | 2     | 1     | 1     | 3     | 8     | 5%  |
| H  | 2     |       | 1     | 1     |       | 1     | 5     | 3%  |
| E  |       |       |       | 2     | 2     |       | 4     | 2%  |
| T  |       |       | 1     | 1     | 2     |       | 4     | 2%  |
| A  | 1     |       |       | 1     | 1     | 1     | 4     | 2%  |
| P  | 1     |       | 1     |       |       | 1     | 3     | 2%  |
| K  | 1     | 1     |       |       | 1     |       | 3     | 2%  |
| Q  |       | 1     |       |       |       | 1     | 2     | 1%  |
| L  | 1     |       | 1     |       |       |       | 2     | 1%  |
| M  |       | 1     |       |       |       | 1     | 2     | 1%  |
| I  |       |       |       |       | 1     |       | 1     | 1%  |
| V  |       |       | 1     |       |       |       | 1     | 1%  |
| C  |       |       |       |       |       |       | 0     | 0%  |
| TOTAL | 30 | 9    | 31    | 22    | 45    | 31    | 168   | 100% |

II. Isolated Nucleic Acid Molecules

One aspect of the invention pertains to isolated nucleic acid molecules that encode polypeptides of the present invention as well as nucleic acid fragments sufficient for use as hybridization probes to identify nucleic acid molecules encoding these polypeptides and fragments for use as PCR primers for the amplification or mutation of the nucleic acid molecules. As used herein, the term "nucleic acid molecule" or "polynucleotide" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention can be isolated using standard molecular biology techniques and the sequence information provided herein. For example, a nucleic acid molecule of the invention can be isolated by the polymerase chain reaction (PCR) using synthetic oligonucleotide primers designed based upon the sequences of the invention.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences of the invention can be prepared by standard synthetic techniques, e.g., using an automated DNA synthesizer.

In another embodiment, an isolated nucleic acid molecule of the invention comprises a nucleic acid molecule which is a complement to a described nucleic acid molecule. A nucleic acid molecule which is complementary to a described nucleic acid molecule, is one which is sufficiently complementary to a described nucleotide sequence, such that it can hybridize to the respective nucleotide sequence of the invention, thereby forming a stable duplex.

In still another embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99% or more identical to the entire length of the nucleotide sequence of the invention, or a portion of any of these nucleotide sequences.

The invention further encompasses nucleic acid molecules that differ from nucleotide sequence(s) that encode polypeptides of the invention due to degeneracy of the genetic code and thus encode the same polypeptides as those encoded by the respective nucleotide sequence. In another embodiment, an isolated nucleic acid molecule of the invention has a nucleotide sequence encoding a polypeptide of the present invention.

Nucleic acid molecules corresponding to homologues of a nucleic acid molecule of the present invention can be isolated based on their homology to the nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising a nucleic acid molecule of the present invention.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further non-limiting example of stringent hybridization conditions includes hybridization at 6×SSC at 45° C., followed by one or more washes in 0.2×SSC, 0.1% SDS at 65° C. A non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH2PO4, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids between 18 and 49 base pairs in length, Tm (° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional non-limiting example of stringent hybridization conditions is hybridization in 0.25-0.5M NaH2PO4, 7% SDS at about 65° C., followed by one or more washes at 0.02M NaH2PO4, 1% SDS at 65° C., see e.g., Church and Gilbert (1984) Proc. Natl. Acad. Sci. USA 81:1991-1995 (or alternatively 0.2×SSC, 1% SDS).

The skilled artisan will further appreciate that changes can be introduced by mutation into a nucleic acid molecule of the present invention, thereby leading to changes in the amino acid sequence of the encoded polypeptides of the present invention, without altering the functional ability of the polypeptides. For example, nucleotide substitutions leading to amino acid substitutions at "non-essential" amino acid residues can be made in a nucleic acid molecule of the present invention. A "non-essential" amino acid residue is a residue that can be altered from a nucleic acid molecule of the present invention without altering the biological property, whereas an "essential" amino acid residue is required for the biological property. For example, amino acid residues that are important for the structural integrity of the antibody molecules, are predicted to be particularly unamenable to alteration.

Accordingly, another aspect of the invention pertains to nucleic acid molecules encoding polypeptides of the present invention that contain changes in amino acid residues that are not essential for activity. Such polypeptides differ in amino acid sequence from those in FIGS. 2-7, yet retain biological activity. In one embodiment, the isolated nucleic acid molecule comprises a nucleotide sequence encoding a polypeptide, wherein the polypeptide comprises an amino acid sequence at least about 71%, 75%, 80%, 85%, 90%, 91%, 92%, 93%, 94%, 95%, 96%, 97%, 98%, 99% or more identical to polypeptides of the invention.

An isolated nucleic acid molecule encoding a polypeptide identical to the polypeptides of the invention can be created by introducing one or more nucleotide substitutions, additions or deletions into the nucleotide sequences of the invention such that one or more amino acid substitutions, additions or deletions are introduced into the encoded polypeptide. Mutations can be introduced into nucleic acid molecules of the present invention by standard techniques, such as site-directed mutagenesis and PCR-mediated mutagenesis. In one embodiment, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide of the invention (e.g., those in FIGS. 2-7) can be replaced with another amino acid residue from the same side chain family. Alternatively, in another embodiment, mutations can be introduced randomly along all or part of a nucleic acid molecule(s) of the present invention, such as by saturation mutagenesis, and the resultant mutants can be screened for biological activity to identify mutants that retain activity. Following mutagenesis of a nucleic acid molecule of the present invention, the encoded polypeptide can be expressed recombinantly and the activity of the polypeptide can be determined.

The expression characteristics of a nucleic acid molecules of the present invention within a cell line or microorganism may be modified by inserting a heterologous DNA regulatory element into the genome of a stable cell line or cloned microorganism such that the inserted regulatory element is operatively linked with the a nucleic acid molecules of the present invention. For example, a heterologous regulatory element may be inserted into a stable cell line or cloned microorganism, such that it is operatively linked with a nucleic acid molecules of the present invention, using techniques, such as targeted homologous recombination, which are well known to those of skill in the art, and described, e.g., in Chappel, U.S. Pat. No. 5,272,071; PCT publication No. WO 91/06667, published May 16, 1991.

III. Isolated Polypeptide Molecules

One aspect of the invention pertains to isolated polypeptides. In one embodiment, polypeptides of the present invention can be isolated from cells or tissue sources by an appropriate purification scheme using standard protein purification techniques. In another embodiment, polypeptides of the present invention are produced by recombinant DNA techniques. Alternatively, polypeptides of the present invention can be chemically synthesized using standard peptide synthesis techniques.

An "isolated" or "purified" polypeptide is substantially free of cellular material or other contaminating proteins from the cell or tissue source from which the polypeptides of the present invention is derived, or substantially free from chemical precursors or other chemicals when chemically synthesized. The language "substantially free of cellular material" includes preparations of polypeptide(s) of the present invention in which the polypeptide is separated from cellular components of the cells from which it is isolated or recombinantly produced. In one embodiment, the language "substantially free of cellular material" includes preparations of polypeptide(s) of the present invention having less than about 30% (by dry weight) of proteins not of the present invention (also referred to herein as a "contaminating protein"), more preferably less than about 20% of proteins not of the present invention, still more preferably less than about 10% of proteins not of the present invention, and most preferably less than about 5% of proteins not of the present invention. When polypeptides of the present invention are recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of polypeptide(s) of the present invention in which the polypeptide is separated from chemical precursors or other chemicals which are involved in the synthesis of the polypeptide. In one embodiment, the language "substantially free of chemical precursors or other chemicals" includes preparations of polypeptide(s) of the present invention having less than about 30% (by dry weight) of chemical precursors or of proteins not of the present invention, more preferably less than about 20% chemical precursors or of proteins not of the present invention, still more preferably less than about 10% chemical precursors or of proteins not of the present invention, and most preferably less than about 5% chemical precursors or of proteins not of the present invention.

In another embodiment, polypeptide(s) of the present invention (e.g., those that encode the lowered affinity antibodies of the present invention) has an amino acid sequence that includes one or more of SEQ ID NO: 1-14.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In one embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, 99.5%, or 99.9% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The amino acid sequences of the described polypeptide(s) will enable those of skill in the art to produce corresponding polypeptides. Such polypeptides can be produced in prokaryotic or eukaryotic host cells by expression of polynucleotides encoding a polypeptide(s) of the present invention. Alternatively, such polypeptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu Rev. Biochem. 57:957; and Offord, R. E. (1980) Semisynthetic Proteins, Wiley Publishing, which are incorporated herein by reference).

IV. Recombinant Expression Vectors and Host Cells

Another aspect of the invention pertains to vectors, preferably expression vectors, containing a nucleic acid molecule encoding a polypeptide of the present invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of polypeptides of the present invention in prokaryotic or eukaryotic cells. For example, the polypeptides can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of polypeptides in prokaryotes is most often carried out in E. coli with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide.

Examples of suitable inducible non-fusion E. coli expression vectors include pTrc (Amann et al. (1988) Gene 69:301-315) and pET 1 Id (Studier et al. (1990) Methods Enzymol. 185:60-89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in E. coli is to express the polypeptide in host bacteria with impaired capacity to proteolytically cleave the recombinant polypeptide (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.).

Alternatively, polypeptides of the present invention (e.g., FIGS. 2-7) can be expressed in insect cells using baculovirus expression vectors. Baculovirus vectors available for expression of polypeptides in cultured insect cells (e.g., Sf9 cells) include the pAc 'series (Smith et al. (1983) Mol. Cell Biol. 3:2156-2165) and the pVL series (Lucklow and Summers (1989) Virology 170:31-39).

In yet another embodiment, a nucleic acid of the present invention (e.g., FIGS. 2-7) is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the .alpha.-fetoprotein promoter (Campes and Tilghman (1989) Genes Dev. 3:537-546).

Another aspect of the invention pertains to host cells into which a nucleic acid molecule of the present invention is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the present invention can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as the polynucleotide of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the present invention. Accordingly, the invention further provides methods for producing a polypeptide of the present invention using the host cells of the present invention. In one embodiment, the method comprises culturing the host cell of the invention (into which a recombinant expression vector encoding a polypeptide of the present invention has been introduced) in a suitable medium such that a polypeptide of the present invention is produced. In another embodiment, the method further comprises isolating a polypeptide of the present invention from the medium or the host cell.

The host cells of the invention can also be used to produce non-human transgenic animals, as described below.

V. Methods of Use

Lowered affinity antibodies can be used in assays designated to diagnostically or prognostically monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

EXAMPLE 1

Generation and Characterization of Novel Lowered Affinity Antibodies

The amino acid sequences of OKT3 complementarity determining regions were modified to reduce or eliminate antigen binding without affecting antibody structure or expression. Exemplary CDR sequences of control antibodies of the invention are listed in Table 3. The resulting lowered affinity antibodies expressed normally (FIG. 3), and had minimal or no capacity to bind to human Jurkat cells (FIG. 4) or human peripheral blood mononuclear cells (PBMCs, FIG. 5).

TABLE 3

Exemplary lowered affinity antibody CDR sequences.

| CDR | Substitution | Sequence | SEQ ID NO. |
|---|---|---|---|
| OKT3 CDRH1 | NA | GYTFTRYTMH | SEQ ID NO: 1 |
| CDRH1m | T33A | GYTFTRYAMH | SEQ ID NO: 2 |
| OKT3 CDRH2 | NA | YINPSRGYTNYNQKFKD | SEQ ID NO: 3 |
| CDRH2m1 | Y50A/N52A/R55A/Y57A | AIAPSAGATNYNQKFKD | SEQ ID NO: 4 |
| CDRH2m2 | R55A | YINPSAGYTNYNQKFKD | SEQ ID NO: 5 |
| OKT3 CDRH3 | NA | YYDDHYCLDY | SEQ ID NO: 6 |
| CDRH3m1 | Y99A/D101A/Y104A | AYADHACLDY | SEQ ID NO: 7 |
| CDRH3m2 | D101A | YYADHYCLDY | SEQ ID NO: 8 |
| OKT3 CDRL1 | NA | SASSSVSY | SEQ ID NO: 9 |
| CDRL1m | S30A/Y31A | SASSSVAA | SEQ ID NO: 10 |
| OKT3 CDRL2 | NA | IYDTSKL | SEQ ID NO: 11 |
| CDRL2m | D49A | IYATSKL | SEQ ID NO: 12 |
| OKT3 CDRL3 | NA | QQWSSNPFT | SEQ ID NO: 13 |
| CDRL3m | W90A/S91A | QQAASNPFT | SEQ ID NO: 14 |

Cell Lines and Media

Human 293T cells were maintained in Dulbecco's Modified Eagles's medium (DMEM) supplemented with 10% fetal bovine serum (FBS) (Invitogen, Gibco, Carlsbad, Calif.), 2 mM L-glutamine, and 40 ug/ml of gentamicin. Mouse OKT3, an anti-human CD3 antibody producing hybridoma cell line, was grown in Iscove's Modified Dulbecco's medium (IMDM) containing 10% FBS, 1 mM sodium pyruvate, 2 mM L-glutamine, and 40 ug/ml of gentamicin. Jurkat E6.1, a human leukemic T cell line, was grown in RPMI medium supplemented with 10% FBS, 2 mM L-glutamine, and 40 ug/ml of gentamicin. All media and supplements were purchased from Lonza, Walkville, Md., except for FBS.

Construction of OKT3 Heavy and Light Chain Expression Plasmids Total RNA was isolated from OKT3 hybridoma cell line using TRIzol Reagent from Invitrogen. cDNA was synthesized using SuperScript™ III Reverse Transcriptase (Invitrogen) and Oligo (dT)12-18 Primer (Invitrogen) (SEQ ID NO: 15). Based on Genbank records of mouse OKT3 heavy chain (Accession #A22261) and light chain (Accession #A22259) nucleotide sequences, the entire coding sequences of the heavy and light chains were amplified via polymerase chain reactions (PCR) with oligo dT-primed cDNA of OKT3 hybridoma as the template, and cloned into a mammalian expression plasmid, driven by CMV Immediate Early gene promoter, called pME. The complete nucleotide sequence of plasmid pME-wtOKT3 HC (FIG. 6) is represented in SEQ ID NO: 23 and the complete nucleotide sequence of plasmid pME-wtOKT3LC (FIG. 7) is represented in SEQ ID NO: 24.

Construction of Expression Plasmids Encoding OKT3 Heavy and Light Chain Variants Site directed mutagenesis was performed using standard PCR techniques to generate the OKT3 heavy and light chain variants, replacing various antigen contacting amino acids within the CDRs with alanine. PCR fragments harboring the mutations were cloned into the same expression plasmid pME. The resultant plasmids were confirmed by sequencing reactions.

Transfection

The OKT3 and variant antibodies were produced by transient transfection using the standard calcium phosphate method. Briefly, 293T cells were seeded in 6-well plates at $6 \times 10^5$ cells/3 ml 293T medium/well 20-24 hours before transfection. 3 hours prior to transfection, the culture medium was changed to IMDM supplemented with 10% FBS, 25 mM Hepes buffer and 40 ug/ml gentamycin. The transfection procedure was carried out by first mixing 8 µg each of the OKT3 heavy and light chain plasmid DNAs with 31 µl of 2M $CaCl_2$ and sterile distilled water for a final volume of 250 µl. The DNA/calcium mixture was then slowly added to 250 µl of 2xHBS buffer (281 mM NaCl, 100 mM HEPES, 1.5 mM $Na_2HPO4$ at pH 7.12). The transfection mixture was incubated at room temperature for 20 minutes, and then added slowly to the 293T cultures. 12-16 hours after transfection, the culture medium was changed once again to the complete 293T medium. 40-48 hours after transfection, culture supernatants containing OKT3 variant antibodies were harvested, and used for subsequent analyses.

Antibody Quantitation

The amount of OKT3 and variant antibodies produced by transient transfection was determined by the Guava RapidQuant mouse IgG Kit (Guava Technologies, Hayward, Calif.) following the manufacture's protocol. In brief, 10 µl of supernatant from each transfection was incubated with IgG capture beads for 40 min with shaking. Subsequently, FITC-conjugated goat anti-mouse IgG was added to each sample and incubated 60 minutes with shaking. The sample volume was brought up to 200 µl and run on Guava EasyCyte system (Guava). The antibody concentration in each sample was calculated by comparing the mean florescence channel (MFI) of the samples with those of the standards.

Isolation of Human Peripheral Mononuclear Cells (hPBMC)

Human peripheral mononuclear cells (hPBMC) were isolated using Ficoll-paque gradient method. In brief, human whole blood was diluted 1:1 with 1× Phosphate Buffered Saline (PBS) and carefully layered on the top of Ficoll-paque (0.4 volume of blood sample volume) (GE Healthcare, Uppsala, Sweden). After centrifugation at 900 g for 30 min, hPBMC at the interface of blood and Ficoll-paque were carefully extracted. Cell suspensions were diluted 1:3 with 1×PBS and spun at 400 g for 10 min at 8-20° C. Cell pellets were washed one more time with 1×PBS at 400 g for 10 min at 8-20° C. and diluted with FACS buffer (PBS with 2% FCS, 0.1% $NaN_3$) for flow cytometric analysis.

Flow Cytometry

Human Jurkat cells ($1 \times 10^5$ cells/well in 96-well plates) or hPBMC ($3 \times 10^5$ cells/well in 96-well plates) were incubated with 100 µl of transfection supernatant of OKT3 and variants at 4° C. for 60 minute and washed twice with 200 µl of FACS buffer. Cells were stained with 100 µl of phycoerythrin (PE)-conjugated goat-anti-mouse Immunoglobulin G (Invitrogen-Caltag, Carlsbad, Calif.) for 60 min at 4° C., and washed twice with 200 ul of FACS buffer. The cells were then fixed with 1% paraformaldehyde for 15 minute at 4° C., and washed once with FACS buffer. Cells were then resuspended in 200 µl of FACS buffer for analysis on a Guava EaseCyte Plus system (Guava Technologies, Inc., Hayward, Calif.).

Binding of OKT3 and OKT3 Variant to Jurkat Cells.

Figure 8:
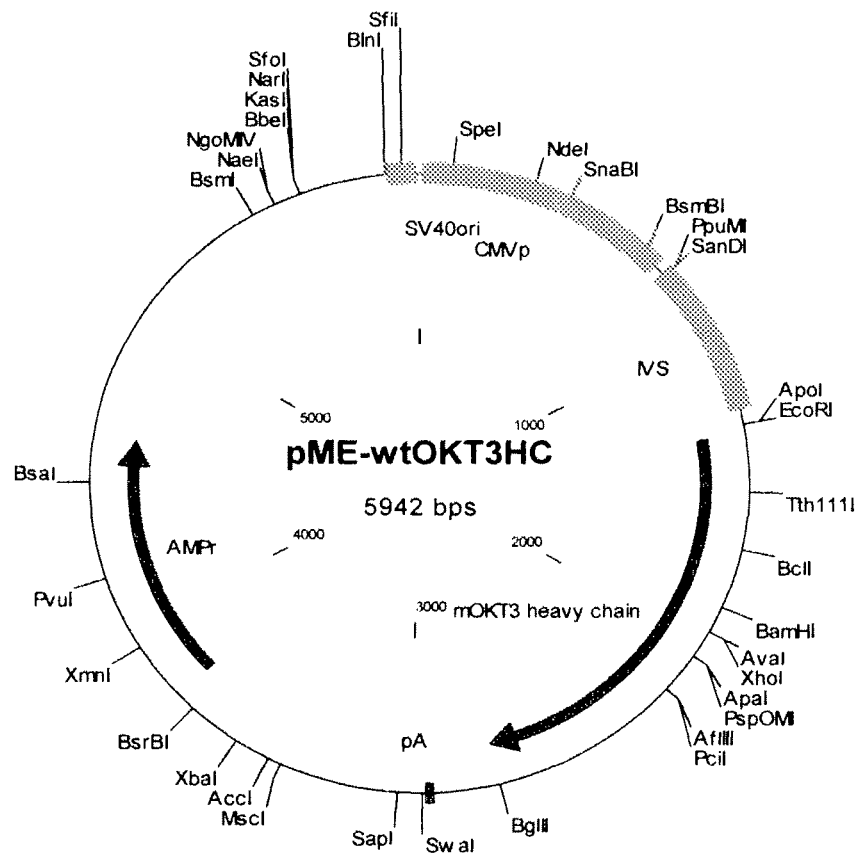
Figure 9:
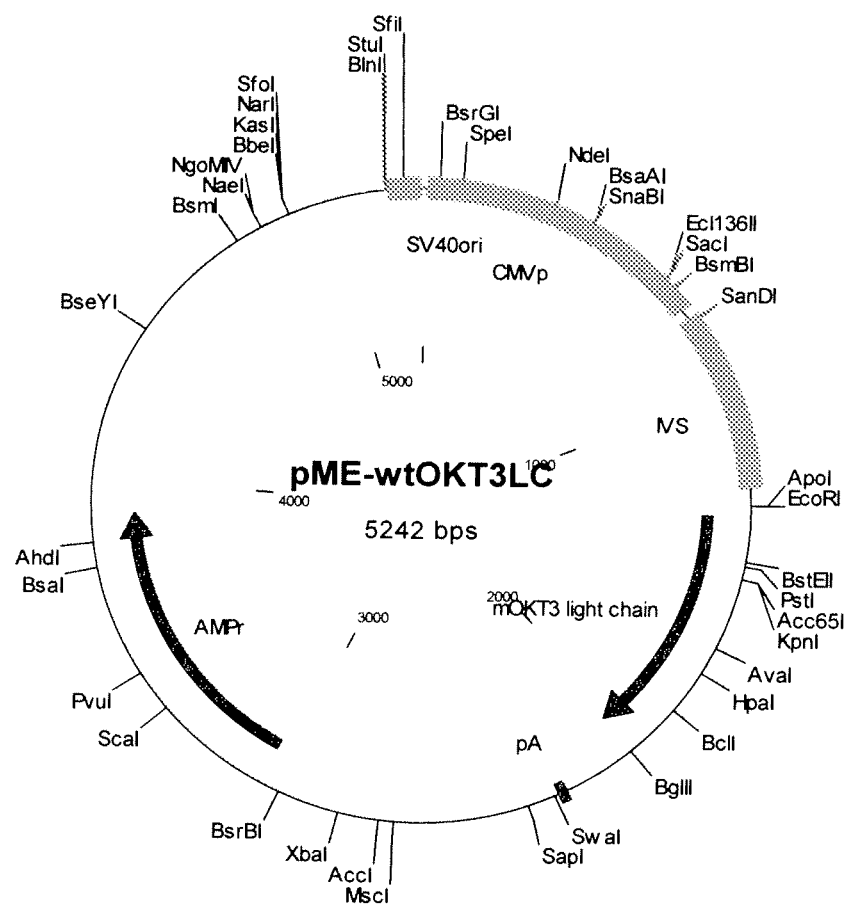
Figure 10:
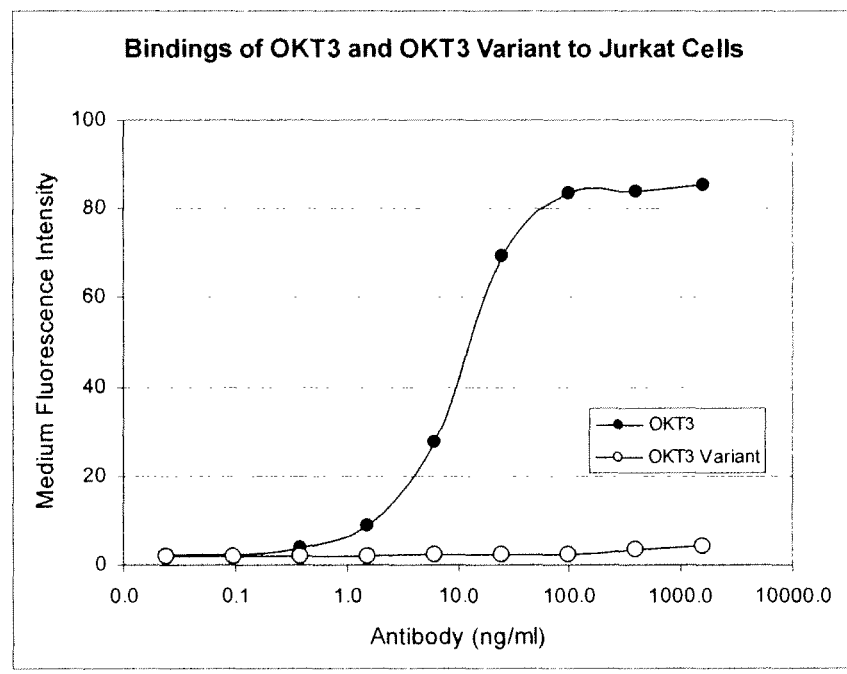
Figure 11:
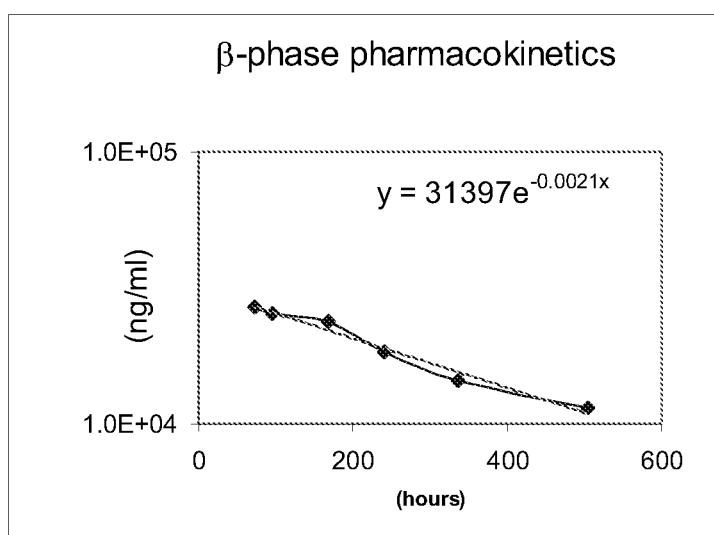

A total of $1 \times 10^5$ Jurket cells were incubated with serially diluted OKT3 or OKT3 variant antibody, followed by PE-conjugated goat anti-mouse IgG, and analyzed by the FACS. At 1600 ng/ml, binding of OKT3 variant is comparable to that of OKT3 antibody at 0.4 ng/ml. Thus, the binding affinity of OKT3 variant is approximately 4000× less than that of the parental OKT3 antibody (FIG. 8).

Pharmacokinetics of the Variant Antibody.

Pharmacokinetic analysis of the variant IgG2a antibody. An IgG2a antibody was produced by co-expressing of a CDR mutated heavy chain (Seq No. 26) and a CDR mutated light chain (Seq No. 47). While it is clear that this variant antibody no longer binds to the CD3 which is the antigen of the parental antibody, OKT3, it is not known whether this antibody may serendipitously interact yet with another antigen(s). One way to test this is to determine if the variant antibody has an in vivo half life similar to endogenous circulating IgG2a antibody. The variant antibody was administered in B6 mice and serum samples were collected up to 21 days. The concentration of recombinant IgG2a antibody was measured by an allotype specific anti-mouse antibody. The half life of the antibody was calculated by fitting the beta-phase of the pharmacokinetic profile and determined to be 13.75 days (FIG. 9). This half life is in close agreement with the reported 10-15 days half life of murine IgG2a antibody (Talbotp, P. J. and Buchmeie M. J. Catabolism of homologous murine monoclonal hybridoma IgG antibodies in mice. Immunology 60:485-489, 1987). The long serum half life indicates that this antibody is not likely to interact with an unexpected antigen(s) and the in vivo system is not able to discriminate this variant antibody from the endogenous immunoglobulin of the same isotype.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for producing a modified antibody or antibody fragment with reduced antigen binding affinity, comprising the steps of:
   a) obtaining information about a target antigen, and a reference antibody having specific binding affinity for the target antigen;
   b) identifying within the CDR regions of the reference antibody using amino acid contact frequency statistics, the binding amino acids tyrosine, serine, asparagine, aspartate, tryptophan or arginine, which are capable of an interaction with the target antigen;
   c) altering at least one of the binding amino acids to eliminate specific binding affinity for the target antigen without substantially altering the overall antibody structure;
   d) expressing the modified antibody in a eukaryotic cell expression system, recovering the modified antibody therefrom and evaluating the productivity of the modified antibody; and
   e) confirming the absence of detectable specific binding of the modified antibody or antibody fragment to the target antigen, as well as any non-target antigen by determining its in vivo half-life.

2. The method of claim 1, wherein the altering of the amino acid in the CDR polypeptide sequence is done by replacing at least one amino acid with a non-interacting amino acid.

3. The method of claim 2, wherein said non-interacting amino acid is selected from the group consisting of: alanine, valine, leucine, isoleucine, proline and methionine.

4. The method of claim 3, wherein said non-interacting amino acid is alanine.

5. The method of claim 1, wherein the step of confirming the absence of detectable specific binding is accomplished by FACS, ELISA, or radioimmunoassay.

6. A method for producing an antibody or antibody fragment with reduced antigen binding affinity, comprising the steps of:
   a) identifying from within the CDR sequences of the antibody or antibody fragment based on amino acid contact frequency statistics, at least one tyrosine, serine, asparagine, aspartate, tryptophan or arginine, which is likely to interact with a target antigen;
   b) altering the antigen interacting CDR amino acid sequence of the antibody or antibody fragment, to reduce antigen binding affinity;
   c) expressing the modified antibody in a eukaryotic cell expression system, recovering the modified antibody or fragment therefrom and evaluating the productivity of the modified antibody or fragment;
   d) confirming the reduced antigen-binding affinity of the modified antibody or antibody ragment has an approximate dissociation constant ($K_D$) of greater than or equal to about $10^{-7}$ M; and
   e) confirming the modified antibody retains an overall antibody structure, an absence of detectable binding to non-target antigen and has an in vivo half-life similar to endogenous circulating antibodies or fragments, thereby confirming lack of binding of the antibody or fragment to non-target antigens.

* * * * *

SEQUENCE LISTING

```
<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Arg Tyr Thr Met His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Arg Tyr Ala Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ile Asn Pro Ser Arg Gly Tyr Thr Asn Tyr Asn Gln Lys Phe Lys
1               5                   10                  15

Asp

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ile Ala Pro Ser Ala Gly Ala Thr Asn Tyr Asn Gln Lys Phe Lys
1               5                   10                  15

Asp

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Tyr Ile Asn Pro Ser Ala Gly Tyr Thr Asn Tyr Asn Gln Lys Phe Lys
1               5                   10                  15
Asp

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Tyr Asp Asp His Tyr Cys Leu Asp Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Tyr Ala Asp His Ala Cys Leu Asp Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Tyr Ala Asp His Tyr Cys Leu Asp Tyr
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ala Ser Ser Ser Val Ser Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ala Ser Ser Ser Val Ala Ala
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Tyr Asp Thr Ser Lys Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Tyr Ala Thr Ser Lys Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Trp Ser Ser Asn Pro Phe Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Ala Ala Ser Asn Pro Phe Thr
1               5

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(18)
<223> OTHER INFORMATION: This sequence may be 12-18 nucleotides in
      length

<400> SEQUENCE: 15
tttttttttt tttttttt                                                 18
```